(12) United States Patent
Kirby

(10) Patent No.: US 12,311,156 B2
(45) Date of Patent: May 27, 2025

(54) PHLEBOTOMY NEEDLE DESTRUCTION

(71) Applicant: Needlesmart Limited, Liverpool (GB)

(72) Inventor: Clifford Ian Kirby, Sefton Village (GB)

(*) Notice: Subject to any disclaimer, the term of this patent is extended or adjusted under 35 U.S.C. 154(b) by 0 days.

(21) Appl. No.: 16/973,915

(22) PCT Filed: Jul. 8, 2019

(86) PCT No.: PCT/EP2019/068273
§ 371 (c)(1),
(2) Date: Dec. 12, 2020

(87) PCT Pub. No.: WO2019/238979
PCT Pub. Date: Dec. 19, 2019

(65) Prior Publication Data
US 2021/0220569 A1    Jul. 22, 2021

(51) Int. Cl.
*A61M 5/32*   (2006.01)
*H05B 1/02*   (2006.01)
*H05B 6/10*   (2006.01)

(52) U.S. Cl.
CPC ........ *A61M 5/3278* (2013.01); *A61M 5/3204* (2013.01); *H05B 1/025* (2013.01); *H05B 6/10* (2013.01); *A61M 2005/3283* (2013.01)

(58) Field of Classification Search
CPC .............. A61M 5/3204; A61M 5/3278; A61M 2005/3283; H05B 1/025; H05B 6/10

USPC .......................................................... 219/635
See application file for complete search history.

(56) References Cited

U.S. PATENT DOCUMENTS

| | | | | |
|---|---|---|---|---|
| 3,313,909 | A * | 4/1967 | Matthews | B23K 11/3063 |
| | | | | 219/86.8 |
| 4,014,323 | A * | 3/1977 | Gilmer | A61B 5/0533 |
| | | | | 607/45 |
| 10,751,527 | B2 * | 8/2020 | Wolf, II | A61N 1/0558 |
| 2020/0376264 | A1* | 12/2020 | Wolf, II | A61N 1/0558 |
| 2022/0287161 | A1* | 9/2022 | Sriram | H05B 7/12 |
| 2023/0201572 | A1* | 6/2023 | Hinman | A61N 1/36002 |
| | | | | 607/115 |

\* cited by examiner

*Primary Examiner* — Eric S Stapleton
(74) *Attorney, Agent, or Firm* — Antoinette M. Tease

(57) ABSTRACT

An apparatus for processing a phlebotomy needle having a double-ended needle with a tub between its tips. The apparatus has a clamping electrode for contacting/clamping one end of the needle between the hub and tip and tip electrode for contacting the needle as its tip. A voltage is applied between the clamping electrode and the tip electrode, to soften/melt the needle via resistive heating, at the same time as the tip electrode is advanced to compress the needle tip and blunt it. The apparatus includes means for allowing the needle to be rotated through so that the first tip and the second tip can be blunted. Also disclosed is means for detaching the needle from a main body and/or for removing a cover covering one end of the needle. The apparatus enables a Vacutainer-type needle to be disassembled into its various parts and the needle rendered blunt and non-hazardous.

20 Claims, 14 Drawing Sheets

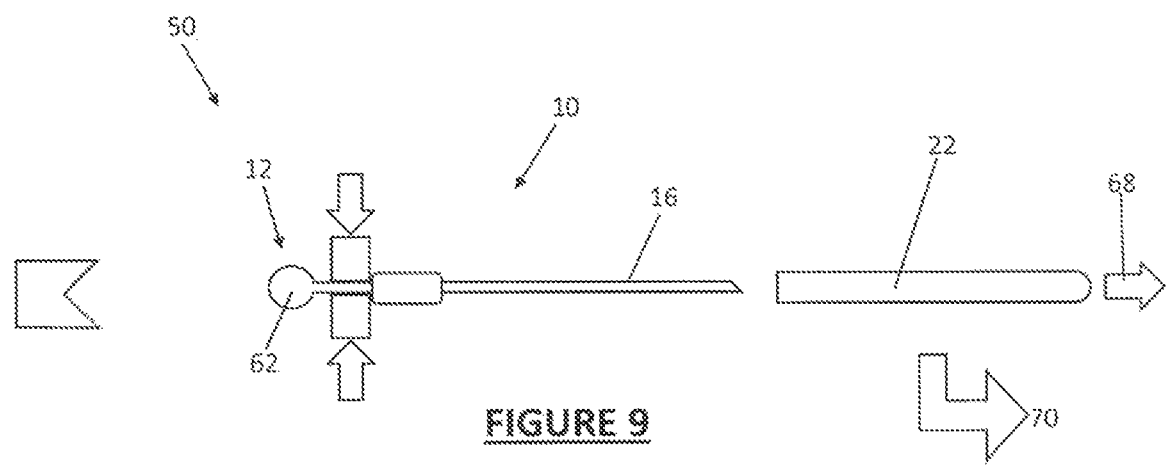
FIGURE 9
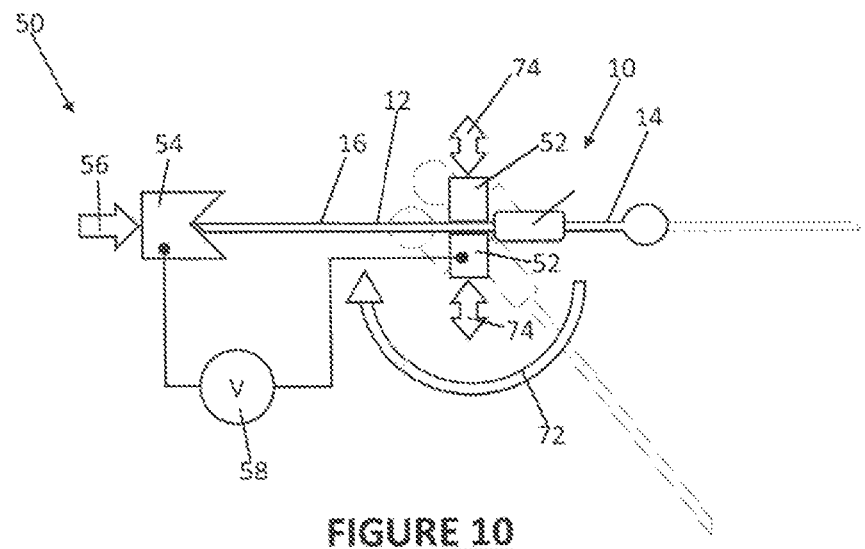
FIGURE 10
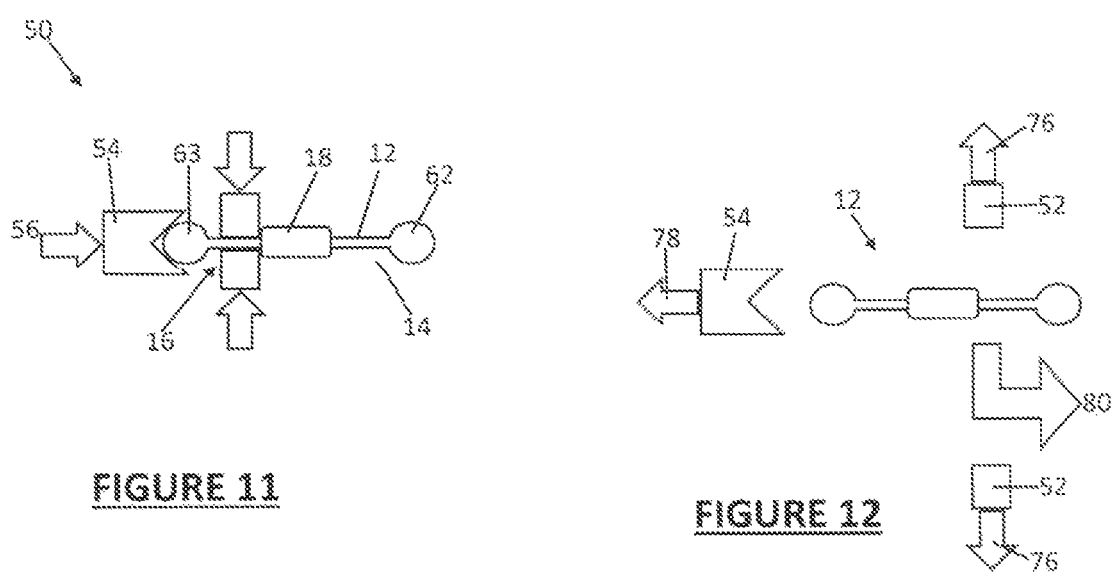
FIGURE 11
FIGURE 12

PHLEBOTOMY NEEDLE DESTRUCTION

This invention relates to an apparatus and method for the safe destruction of used phlebotomy needles.

A phlebotomy needle is a type of hypodermic needle that is used in medicine for taking a sample of blood (or other fluids) from a human or animal patient. A phlebotomy needle differs from a conventional hypodermic needle insofar as it is double-ended. The term "phlebotomy needle" is used herein to describe double-ended needles generally, but they may by used for other purposes than taking blood samples, and the scope of this disclosure is to be construed accordingly to cover other uses of double-ended needles.

A conventional hypodermic needle has a hub at one end, which connects to a syringe or a tube, for example via a luer connector or a push fit connector. The syringe or tube can be used for injecting or withdrawing liquid substances into or from a patient's circulatory system in a manner that is well understood. The actual needle of a hypodermic needle comprises a fine metal tube with a sharp end, which is adapted, in use, to pierce the patient's skin and, in most cases, enter a blood vessel for the delivery of a liquid medicament, or the extraction of a fluid, as the case may be. Once used, a hypodermic needle needs to be disposed of safely because the needle becomes contaminated during use. If a medical practitioner inadvertently suffers a "needle stick injury", i.e. if he/she pierces their own skin with a contaminated needle, then there is a risk of disease/infection being passed from the patient to the medical practitioner.

Various methods of disposing of hypodermic needles are known, for example, the use of "sharps bins" into which used/contaminated needles are placed. A sharps bin generally comprises a pierce-resistant main body, which prevents, or inhibits, the contaminated needle points from coming into contact with people. The sharps bin usually has an obstructed opening that permits needles to be placed into the main body, but which prevents or restricts a user from placing their hand or other body parts into the main body.

Other methods of hypodermic needle destruction are disclosed in, for example, published PCT application number WO2015/011443. In this disclosure, the sharp end of the needle is inserted into a device, whereupon a current is passed through the needle to soften/melt its tip. Axial compression of the needle, whilst in the softened/melted state causes the needle tip to be deformed into a blunt ball, which prevents the formerly sharp tip from posing a needle-stick injury. Moreover, hypodermic needle destruction devices of this general type also have the advantage of heating the needle to or near its melting point, the heat of which destroys any viruses, bacteria and contaminants. Devices of this general type therefore offer two-fold protection, that is: blunting and sterilising the needle. It will be appreciated from the foregoing, that devices and methods for the disposal of hypodermic needles are well-known.

However, this invention is related to the destruction of phlebotomy needles, which are double ended, and which are generally unsuited to the usual forms of disposal and/or destruction, such as would be used for hypodermic needles.

The main issue with phlebotomy needles is that they are relatively complicated devices compared with hypodermic needles. A phlebotomy needle has a double-ended needle, which is mounted somewhere along its mid-section to a hub, which is typically formed from a plastics tube affixed to the exterior surface of the needle by a bead of adhesive, such as epoxy resin. The hub typically has formations for connecting it to a receptacle into which a vacuum container can be inserted. The method of use of a phlebotomy needle is also somewhat different to that of a hypodermic needle. Specifically, the first end of the phlebotomy needle is used to pierce the patient's skin and enters, in use, a blood vessel, such as a vein or artery. Meanwhile, the other end of the needle is subsequently piercingly inserted into a vacuum container, which comprises a hollow, evacuated, sterile receptacle having a pierceable closure at one end. The vacuum receptacle is placed into a housing formed as part of the phlebotomy needle, and upon pushing it home, the other end of the phlebotomy needle pierces the pierceable closure of the vacuum container such that the vacuum within the container is now in fluid communication with interior of the needle. The vacuum within the container thus causes a blood (or other fluid) sample to be drawn up through the hollow interior of the needle, which is dispensed into the container. Once a sample has been obtained, the vacuum container is withdrawn and the pierceable closure self-closes to form a seal, thereby sealing the sample inside.

As previously mentioned, the phlebotomy needle has a housing connected to its hub and the housing is shaped and configured so as to shield sharp tip at the second end of the phlebotomy needle. This housing reduces the likelihood of the medical practitioner inadvertently sustaining a needle-stick injury during the procedure of obtaining a blood sample, as well as providing a location for correctly aligning and placing the vacuum container, in use.

When it comes to disposing of a phlebotomy needle, the standard practice is to simply deposit the entire needle, including its hub and main body into a sharps bin for subsequent incineration/disposal. However, the volume of the phlebotomy needle is quite large and therefore a phlebotomy sharps bin can be filled relatively quickly.

In many phlebotomy departments, a phlebotomist may perform a hundred or so blood tests in any given day, which results in several hundred phlebotomy needles needing to be disposed of, per phlebotomist, per day. Due to the volume of the phlebotomy needles themselves, this creates a significant waste disposal problem.

Furthermore, because the first end of the phlebotomy needle is often not protected in any way, once its cover has been removed, there exists a finite risk of the medical practitioner (the phlebotomist) sustaining a needlestick injury between the time of taking the blood sample and safely disposing of a phlebotomy needle in the sharps bin. A need therefore exists for a solution to this problem.

It may be possible to use a hypodermic needle destruction device, such as that described in published PCT application number WO2015/011443, to partially render safe a phlebotomy needle, that is to say by melting the first end of the phlebotomy needle into a blunt ball, but that only solves part of the problem. Specifically, the main body of the phlebotomy needle still continues to occupy a relatively large amount of space and, furthermore, there is also a finite risk of the second end of the phlebotomy needle posing a needle stick injury hazard to the phlebotomist.

A further problem that exists with phlebotomy needles is the waste stream, which comprises the metal of the needle, the epoxy resin/plastic of the hub, as well as the plastic of the main body of the phlebotomy needle. In addition, certain types of phlebotomy needle comprise a rubber sleeve covering the second end of the needle, the purpose of which will be described below. However, the provision of a rubber needle cover introduces a yet further material that needs to be handled in the waste stream. When these materials are "co-mingled", recycling of these various components is extremely difficult-especially where a biohazard is involved as well.

A need therefore exists for a solution to one or more of the above problems, which this invention aims to provide.

Various aspects of the invention are set forth in the appended claims.

According to a first aspect of the invention, there is provided an apparatus for processing a phlebotomy needle, the phlebotomy needle comprising: a double-ended needle having a first end terminating in a first tip, and a second end terminating in a second tip; and a hub affixed to the needle at a location between the first tip and the second tip, the apparatus comprising: a clamping electrode for contacting and clamping the first or second end of the needle at a position located between the hub and the first or second tip, respectively; a tip electrode for contacting the needle at its first or second tip, respectively; means for applying a voltage between the clamping electrode and the tip electrode, such that an electric current passes through the respective first or second end of the needle between the clamping electrode and the tip electrode, which current results, in use, in Ohmic heating, which heats and softens or melts the respective first or second tip of the needle; and means for applying a force to the tip electrode so as to cause it, as the tip of the needle softens or melts, to move towards the hub of the needle substantially parallel to an axis of the needle.

The invention therefore provides a means for treating both ends of the double-ended needle part of a phlebotomy needle. The treatment of both ends of the double-ended needle part of a phlebotomy needle may be performed sequentially, substantially simultaneously, or simultaneously.

Where the treatment of both ends of the double-ended needle part of a phlebotomy needle is performed substantially simultaneously, or simultaneously, this can be by way of treating each end of the needle using a respective set of clamping/tip electrode pairs.

As such, the apparatus may comprise: a first clamping electrode for contacting and clamping the first end of the needle at a position located between the hub and the first tip; a first tip electrode for contacting the needle at its first tip; means for applying a voltage between the first clamping electrode and the first tip electrode, such that an electric current passes through the first end of the needle between the first clamping electrode and the first tip electrode, which current results, in use, in Ohmic heating, which heats and softens or melts the first tip of the needle; and first means for applying a force to the first tip electrode so as to cause it, as the first tip of the needle softens or melts, to move towards the hub of the needle substantially parallel to an axis of the needle; and further comprising: a second clamping electrode for contacting and clamping the second end of the needle at a position located between the hub and the second tip; a second tip electrode for contacting the needle at its second tip; means for applying a voltage between the second clamping electrode and the second tip electrode, such that an electric current passes through the second end of the needle between the second clamping electrode and the second tip electrode, which current results, in use, in Ohmic heating, which heats and softens or melts the second tip of the needle; and second means for applying a force to the second tip electrode so as to cause it, as the second tip of the needle softens or melts, to move towards the hub of the needle substantially parallel to an axis of the needle.

Additionally or alternatively, where the treatment of both ends of the double-ended needle part of a phlebotomy needle is performed sequentially, this can be by way of treating one end of the needle using a clamping/tip electrode pair, and then by reorienting the needle so as to treat the other end of the needle using the same clamping/tip electrode pair. Means for reorienting the needle may therefore be provided.

As such, the apparatus may comprise: a clamping electrode for contacting and clamping the first end of the needle at a position located between the hub and the first tip; a tip electrode for contacting the needle at its first tip; means for applying a voltage between the clamping electrode and the tip electrode, such that an electric current passes through the first end of the needle between the clamping electrode and the tip electrode, which current results, in use, in Ohmic heating, which heats and softens or melts the first tip of the needle; and means for applying a force to the tip electrode so as to cause it, as the first tip of the needle softens or melts, to move towards the hub of the needle substantially parallel to an axis of the needle; the apparatus further comprising: means for reorienting the phlebotomy needle such that its second end faces towards the tip electrode, and means for releasing the clamping electrode from the first end of the needle and causing the clamping electrode to contact and clamp the second end of the needle at a position located between the hub and the second tip, such that the tip electrode contacts the needle at its second tip and wherein the means for applying the voltage applies the voltage between the clamping electrode and the tip electrode, such that an electric current passes through the second end of the needle between the clamping electrode and the tip electrode, which current results, in use, in Ohmic heating, which heats and softens or melts the second tip of the needle; and wherein the means for applying a force to the tip electrode causes the second tip, as it softens or melts, to move towards the hub of the needle substantially parallel to an axis of the needle.

The means for reorienting the phlebotomy needle suitably comprises a rotational actuator adapted to rotate the phlebotomy needle through substantially 180-degrees about a point centred substantially on the centre of the hub. Such a configuration enables both ends of the needle to be treated using a common clamping/tip electrode pair. Further, by rotating the needle, as opposed to moving the clamping/tip electrode pair, the apparatus can be simplified.

In certain embodiments, the means for reorienting may comprise a turntable. The phlebotomy needle can be mounted on the turntable, and thereby rotated though any desired angle, for example, 180 degrees, by rotating the turntable.

The means for releasing the clamping electrode from the first end of the needle and causing the clamping electrode to contact and clamp the second end of the needle at a position located between the hub and the second tip may, in certain embodiments, comprise means for axially displacing the phlebotomy needle relative to the clamping electrode, such that the clamping electrode is able to clamp the phlebotomy needle on either side of the hub. This configuration may be useful insofar as it enables the apparatus to be rationalised somewhat, by only requiring one set of clamping electrodes. However, by axially displacing the phlebotomy needle mid- or part-way through the process, this may result in inadvertent displacement or misalignment of the phlebotomy needle, thereby potentially degrading subsequent processing steps.

As such, a preferred embodiment of the invention sees the means for releasing the clamping electrode from the first end of the needle and causing the clamping electrode to contact and clamp the second end of the needle at a position located between the hub and the second tip comprising a pair of clamping electrodes, one located on either side of the hub. Thus, the phlebotomy needle can be clamped, as desired, at either the first or second end of the needle at will, without having to actually move the phlebotomy needle relative to the camping electrode to do so.

The clamping electrode may take any suitable form, but in certain embodiments, it comprises two or more opposing metal jaws which move towards each other so as to clamp a portion of the needle therebetween.

The clamping electrode is suitably adapted to clamp the needle near to the hub. There is a compromise here, however, insofar as if the clamping electrode clamps the needles too far from the hub, the amount of needle deformation that this possible, and hence the amount of axial compression of the needle may be limited. On the other hand, clamping the needle very close to the hub can cause undesirable overheating of the hub as heat is conducted through the needle beyond the clamping electrode. As such, the needle should ideally be clamped sufficiently close to the hub so as to maximise the amount of axial compression of the needle during the treatment; but at the same time, sufficiently far away from the hub so that the heat conducted through the needle, beyond the clamping electrode and towards the hub, is insufficient to damage, over-heat and/or burn the hub and/or the grout/adhesive, which bonds the hub to the needle. Therefore, clamping electrode can be adapted to grip the needle at any one or more of the positions from the group comprising: within 10 mm of the hub; within 5 mm of the hub; within 2 mm of the hub; within 1 mm of the hub; and more than 1 mm from the hub.

Preferably, the tip electrode comprises a concave surface. Such a configuration may provide a guide for the tip of the needle, for centralising the tip of the needle with the tip electrode. This configuration may suitably serve to keep the alignment of the needle parallel to the direction of travel of the tip electrode, in use.

The means for applying a voltage may be of any suitable type. Typically, however, it comprises any one or more of the group comprising: a DC power supply; an AC power supply; and an RF power supply. The power supply may be a continuous power supply, or in certain embodiments, it may provide a pulsed AC, DC or RF voltage between the clamping and tip electrodes. In certain embodiments of the invention, where both ends of the needle are treated by respective clamping/tip electrode pairs, the means for applying a voltage may be adapted to alternately apply a voltage: between the first clamping and first tip electrodes; and between the second clamping and second tip electrodes.

Preferably, the Ohmic heating of the needle, during the processing thereof, is sufficient to cause decontamination, but preferably, sterilisation of the needle. This may comprise the Ohmic heating causing the needle to be heated to greater than 100° C., greater than 200° C., greater than 250° C. or greater than 300° C., which would be sufficient to kill, or at least neutralise, any pathogens, viruses, bacteria thereon or therein. In reality, the needle close to the tip electrode typically reaches a much higher temperature, say around 1300 degrees Centigrade, which is more than sufficient to both soften/melt the tip, and to sterilise it.

Force is suitably applied to the tip electrode using a linear actuator or pulley system, which acts axially on the tip electrode in a direction that is parallel to the axis of the needle.

In a preferred embodiment, the apparatus is automated. As such, the apparatus may comprise: an axial conveyor, which carries a turntable upon it, the turntable being configured to rotate about an axis, the turntable carrying a pair of clamping electrodes, each being mounted on actuators so that they can be moved together or apart, as necessary, the tip electrode being mounted on a linear actuator and being aligned, when the axial conveyor is in a first position, with the midpoint of the clamping electrodes.

Where the phlebotomy needle comprises a main body affixed to the hub, the apparatus may further comprise means for detaching the main body from the hub. The means for detaching the main body from the hub suitable comprises a linear actuator adapted to apply an axial stress to the main body, so as to shear the main body from the hub. Additionally or alternatively, the means for detaching the main body from the hub may comprise a rotary actuator adapted to apply a torque to the main body so as to unscrew it from the hub. The means for detaching the main body from the hub, in certain embodiments, is suitably mounted on the turntable.

Where the phlebotomy needle comprises a cover fitted over the second end of needle, the apparatus may further comprise means for detaching the cover from the second end of the needle. The means for detaching the cover from the second end of the needle suitably comprises a pinch and pull actuator, i.e. an actuator that comprises a plurality of grips adapted, in use, to grip the cover, and where the grips are axially displaceable, in use, so as to apply an axial tension to the cover so as to detach it from the second end of the needle.

In order to facilitate the downstream processing of waste, the apparatus may further comprise a plurality of waste stream apertures. This configuration suitably facilitates separating the various components of the phlebotomy needle into different waste streams. Optionally, each waste stream aperture may lead to a chute or other guide/conduit, which causes the various components to be deposited into different receptacles, but the chutes/guide conduits may, in certain instances, simply lead to a common waste collection receptacle.

Various embodiments of the invention shall now be described, by way of example only, with reference to the accompanying drawings in which:

FIGS. 6 to 12 are a sequence showing how the phlebotomy needle shown in FIG. 1 can be disposed of using the apparatus/method of the invention;

Figure 1:
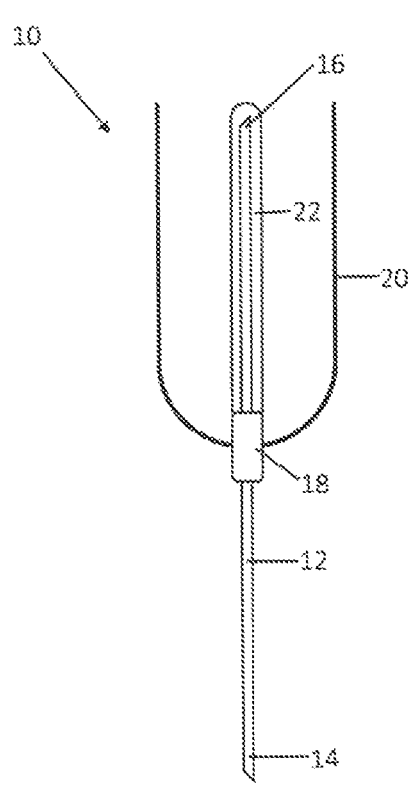
FIG. 1 is a schematic cross-sectional view of a known phlebotomy needle.
Figure 22:
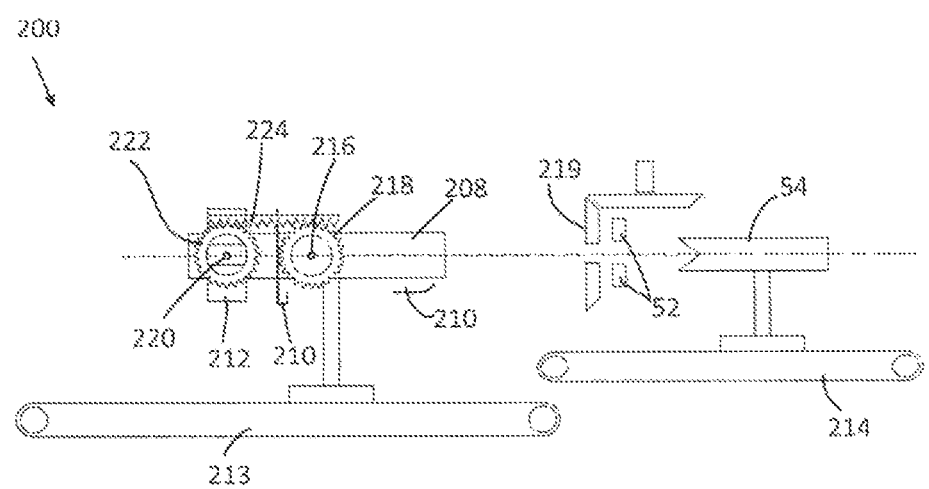
FIG. 22 is a schematic side view of a phlebotomy needle destructions apparatus in accordance with the invention.

FIGS. 25 to 44 are a sequence showing a possible mode of operation of the apparatus shown in FIG. 22; and Referring to FIG. 1 of the drawings, a phlebotomy needle 10 comprises a double-ended needle 12 having a first end 14 and a second end 16. Affixed to a mid-portion of the needle 12 is a hub 18, which is a plastics sleeve bonded to the needle 12 by an adhesive bead, such as an epoxy resin (not shown). Mounted on the hub 18 is a main body 20, which is a closed-ended tube of plastics material, which screw-threadingly connects to the hub 18, or push-fits onto the hub, although the particular connection method is not pertinent to this disclosure. The second end 16 of the needle 12 has a rubber cover 22 over it, whose use shall be explained in greater detail below.

Figure 2:
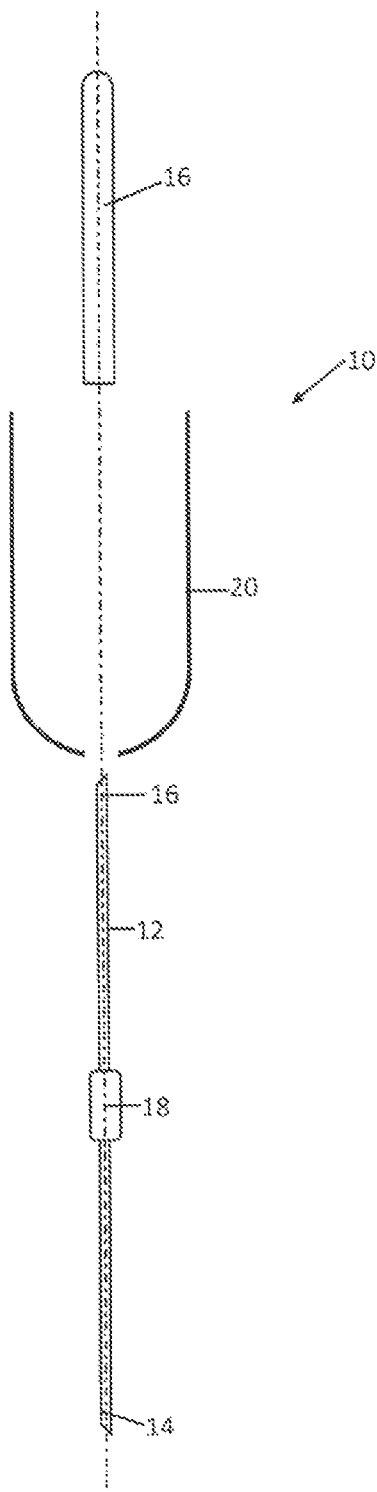
FIG. 2 is an exploded view of the known phlebotomy needle of FIG. 1.

FIG. 2 is simply an exploded view of the known phlebotomy needle 10 shown in FIG. 1.

Figure 3:
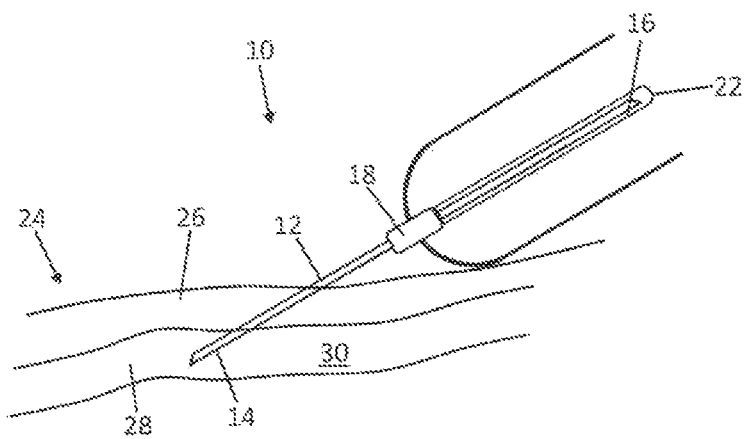
FIGS. 3, 4 and 5 are a sequence showing how the phlebotomy needle of FIG. 1 is typically used.
Figure 4:
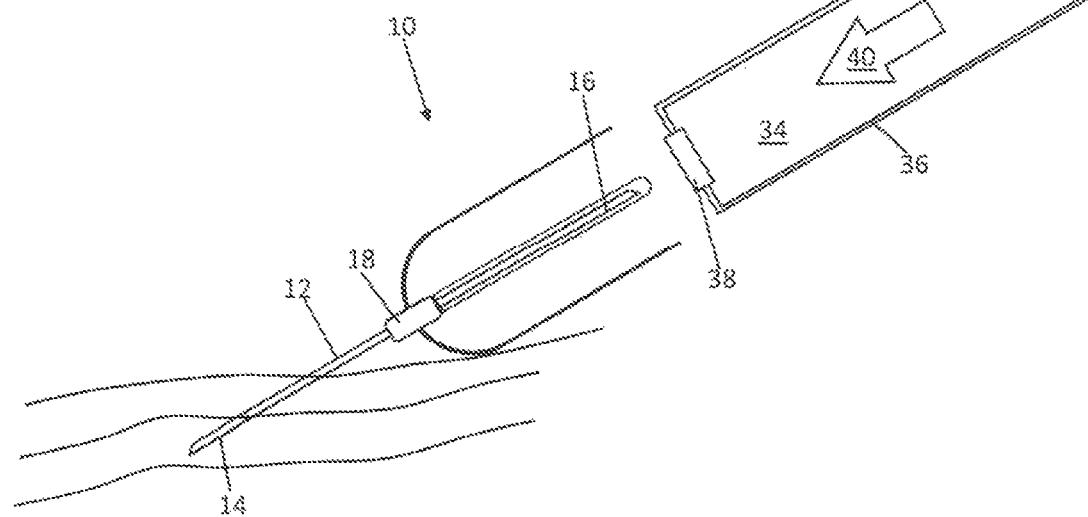
Figure 5:
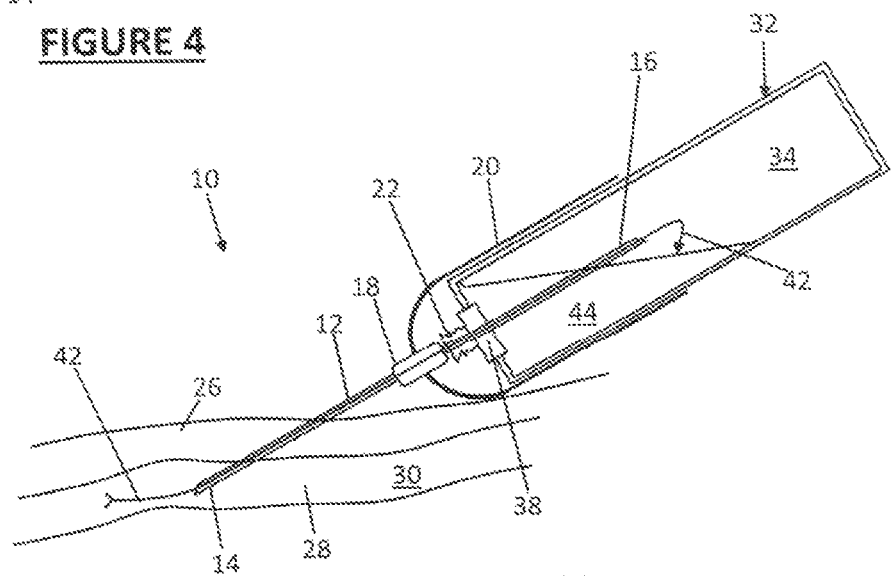

Referring now to FIGS. 3, 4 and 5 of the drawings, the known phlebotomy needle 10 is used as follows. Firstly, the first end 14 of the needle 12 is un-capped (the cap is not shown for clarity) and is inserted into the body of a human or animal patient 24. The patient has a skin or tissue layer 26 below which is a tubular blood vessel 28. The first end 14 of the needle 12 pierces the skin-tissue 26 and is positioned with its tip 14 within the blood vessel 28. The pressure of the blood 30 within the blood vessel 28 causes blood to flow up through the needle 12, but it is prevented from squirting out of the second end 16 of the needle by the rubber cover 22, which prevents egress of blood.

Next, as shown in FIG. 4, a vacuum container 32 is offered up to the phlebotomy needle 10. The vacuum container 32 has an evacuated interior volume 34 enclosed by a hollow, cylindrical main body 36. One end of the vacuum container 32 comprises a pierceable bung 38, which can be pierced by the second end 16 of the needle 12 when it is pushed home 40.

As can be seen with reference to FIG. 5 of the drawings, the second end 16 of the needle 12 pierces the bung 38 and upon pressing 40 the vacuum container 32 home, the second end of the needle 16 pierces the rubber cover 22 which collapses axially—as shown in FIG. 5 of the drawings. Meanwhile, the bung 38 forms a seal around the exterior of the second end 16 of the needle 12. In addition, the vacuum within the interior 34 of the vacuum container 32 now causes blood 44 to be drawn up 42 through the needle 12 to be retained in the interior volume 34 of the vacuum container. It will be noted that the shape and configuration of the main body 20 of the phlebotomy needle 10 serves to guide and support the vacuum container 32 during its insertion, use and subsequent removal.

It will be appreciated, by the skilled reader, that upon subsequent withdrawing of the vacuum container 32 from the phlebotomy needle 10, that the bung 38 self-closes as it passes the tip 16 of the needle, thereby sealing a blood sample 44 inside the interior volume 34 of the vacuum container 32. Moreover, upon withdrawing the vacuum container 32 from the main body 20 of the phlebotomy needle 10, the rubber cover 22 tends to spring back to its original configuration, such as shown in FIG. 4 of the drawings, albeit with a small through hole at its end—where the needle previously pierced it. However, because the cover 22 is manufactured of a rubber material, it too tends to self-close upon withdrawal of the vacuum container 32 thereby re-sealing the second end 16 of the needle 12 and thus stopping blood 30 from squirting out through the second end 16 of the needle 12 when the vacuum container 32 has been removed and a blood sample taken.

It will also be understood by the skilled reader that the same phlebotomy needle can be used to obtain several samples-simply by using a second, third or more vacuum containers 32 in sequence with the needle 10 kept in situ.

Once sufficient samples have been taken, the phlebotomy needle 10 can be withdrawn from the patient's skin 16 and pressure applied to stop bleeding. Thereafter, the phlebotomy needle 10 needs to be disposed of safely if its first end 14 or its second end 16 are not to pose a needlestick injury hazard to the phlebotomist.

Turning now to the invention, which is described with reference to FIGS. 6 to 27 of the drawings:

In FIGS. 6 to 12 of the drawings a schematic sequence of how the invention might work is shown—although it will be appreciated that the order of the various steps may be changed and the order of the following steps in the description that follows is not limiting of the invention.

Figure 6:
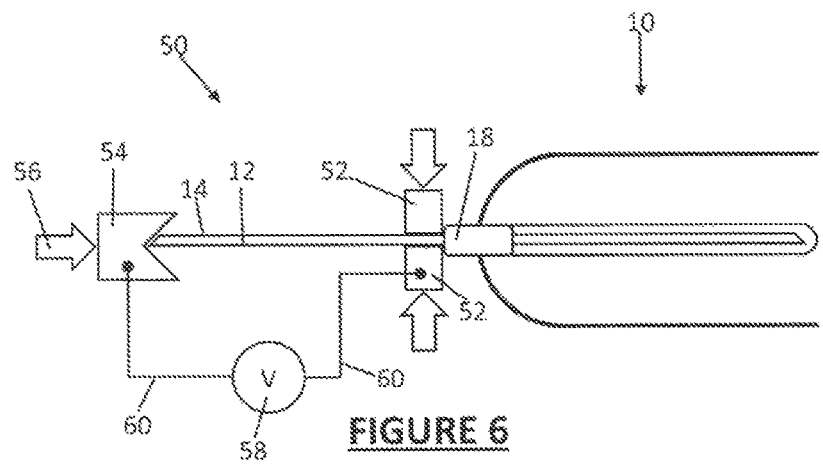

Referring to FIG. 6 of the drawings, the phlebotomy needle 10, as previously described, is inserted into an apparatus 50, where one or more clamping electrodes 52 grip the needle 12 near to the hub 18 and hold it in position. The first end 14 of the needle 12 is thus clamped by the clamping electrodes 52, which are made of metal so as to be able to conduct an electric current into the second end 14 of the needle 12 as shall be described below.

A tip electrode 54 is offered up to the tip of the first end 14 of the needle 12 and an axial force 56 is applied so that the tip electrode 54 abuts the tip of the needle 12.

Typically, the tip electrode 54 is made of metal so as it can provide a current path through the needle between the clamping electrodes 52 and the tip electrode 54. Typically, the tip electrode 54 has a concave end so as to maintain the correct alignment of the needle 12 during the subsequent processing step.

A containment cylinder (not shown) may be provided around the needle 12 so as to prevent it from flexing or bowing under the application of the axial stress 56. The use of a containment cylinder, or indeed a heated containment cylinder, is described in published PCT application number WO2015011443, the entire teaching of which is incorporated herein by reference.

A voltage 58 is applied, e.g. via a pair of fly leads 60, between the clamping electrodes 52 and the tip electrode 54 such that a current passes through the needle 12. The current within the needle results in Ohmic heating of the needle 12, which causes its tip to soften, and subsequently melt. Due to the axial compression 56 applied to the tip electrode during the heating/softening/melting process, the needle 12 is axially deformed and its tip is melted into a blunt ball 62—as shown in FIG. 7 of the drawings.

The heating, softening or melting and deformation of the needle 12 in this way is particularly advantageous because the heat within the needle is sufficient to kill bacteria, pathogens, viruses and other contaminants; whilst at the same time, the axial compression converts the previously sharp tip of the needle 12 into a blunt ball 62—thereby rendering it "safe" from a needlestick injury point of view.

Figure 7:
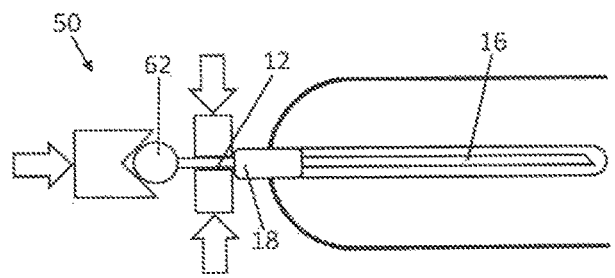

In other words, by way of the process shown in FIGS. 6 and 7 of the drawings, the first end 14 of the needle 12 is rendered "safe"—but that still leaves the second end 16 of the needle to be dealt with.

Figure 8:
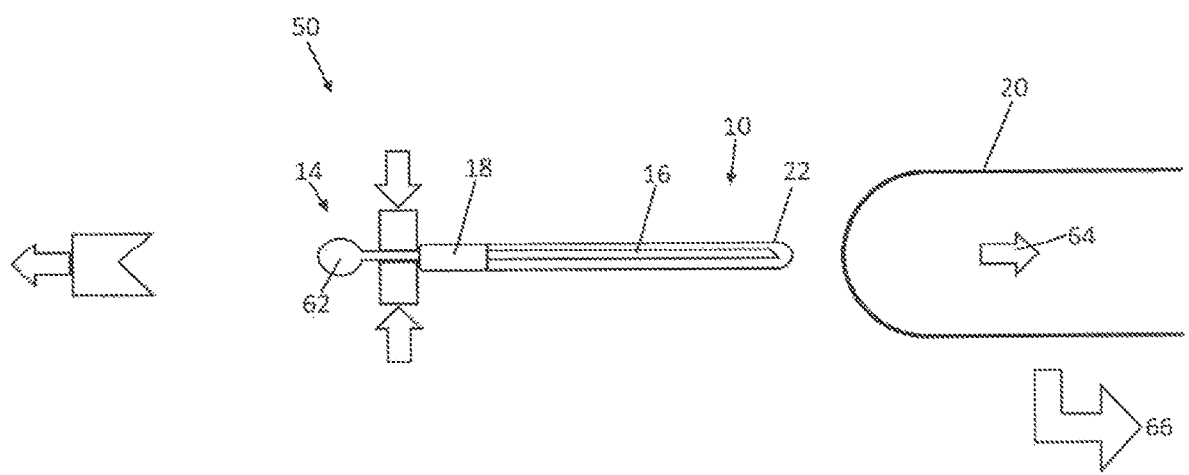

Turning now to FIG. 8 of the drawings, another or the next step in the procedure is to remove 64 of the main body 20 of the phlebotomy needle 10 and this can be achieved relatively easily either by unscrewing it, or by simply applying an axial force in the direction of arrow 64 so as to shear it away from the hub 18. This leads, as can be seen in FIG. 8 of the drawings, to the phlebotomy needle 10 with a blunt first end, a hub 18 and the second end 16 still covered by the rubber cover 22. The main body 22 of the phlebotomy needle 10 can be disposed of 66 into a first waste stream for example, a plastics recycling waste stream, if required/necessary.

Turning now to FIG. 9 of the drawings, the rubber cover 22 can be removed from the second end 16 of the needle 10 via a "pinch and pull" type process, indicated, schematically, by arrow 68 in FIG. 9. Likewise, the rubber cover 22 can be disposed of via a second waste stream 70, namely a rubber waste stream, if necessary and/or desired.

At this point, the phlebotomy needle 10 comprises a first end 12, which has been blunted into a ball 62 and an exposed, sharp second end, which also needs to be rendered safe. To achieve this, a melting process, such as that described above in relation to FIGS. 6 and 7 can be employed using a further tip electrode 54 and further voltage supply 68.

However, for convenience, and in order to avoid duplication of parts, the invention proposes to rotate 72 the needle 10 through 180 degrees and to offer it up to the same tip electrode 54 that was used previously. An axal compression 56 and a voltage 58 can be applied to melt the second end 16 of the needle 12 into a blunt ball 63, as shown in FIG. 11.

However, if the clamping electrodes 52 are used as they were before, namely gripping the first end 14 of the needle, 12, then it has been found that the epoxy bead, which bonds the hub 18 to the needle 12 can burn due to the heating of the needle during the softening/melting process.

The solution to this problem, as proposed by the invention, it so re-grip the needle at a second position. That is, the needle 12 is clamped at its second end 16, close to the hub 18, and this involves simply opening up and then reclosing 74 the clamping electrodes 52 so as to grip the needle 12 on its second end 16, rather than at its first end 14. The effect of this is that the electric current pathway does not pass through the part of the needle 12 which is surrounded by the hub 18, and so heating of the hub 18 is minimised.

The result is shown in FIG. 11 of the drawings, namely a needle 12 with its first end 14 melted into a blunt ball 62, and its second end 16 melted into a similar blunt ball 63.

Next, as shown in FIG. 12, by withdrawing 76 the clamping electrodes 52 and by withdrawing 78 the tip electrode 54, the now-safe needle 12 can be disposed of via a further waste stream 80 if necessary, or desired.

It will be appreciated from the foregoing description that the invention provides a means for safely disposing of phlebotomy needles 10 in a manner that has hitherto not been contemplated. A variation of the phlebotomy needle destruction method described in relation to FIGS. 6 to 12 of the drawings is shown in FIGS. 13 to 18 of the drawings.

Figure 13:
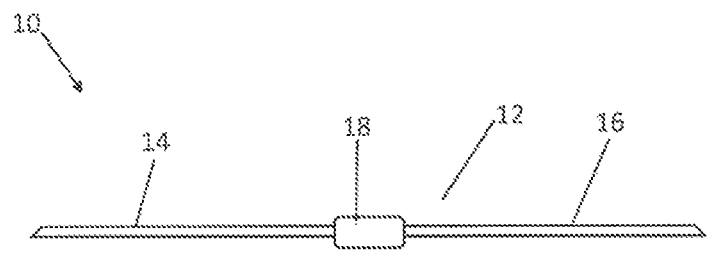
FIGS. 13 to 18 show a schematic sequence of a destruction method in accordance with an aspect of the invention.

Here, as can be seen in FIG. 13, the rubber cover 22 and the main body have been removed from the phlebotomy needle 10, for example using the axial removal method described previously-leaving just a needle 12, with a sharp first end, a sharp second 18 16 and its hub 18 secured somewhere along its midpoint.

Figure 14:
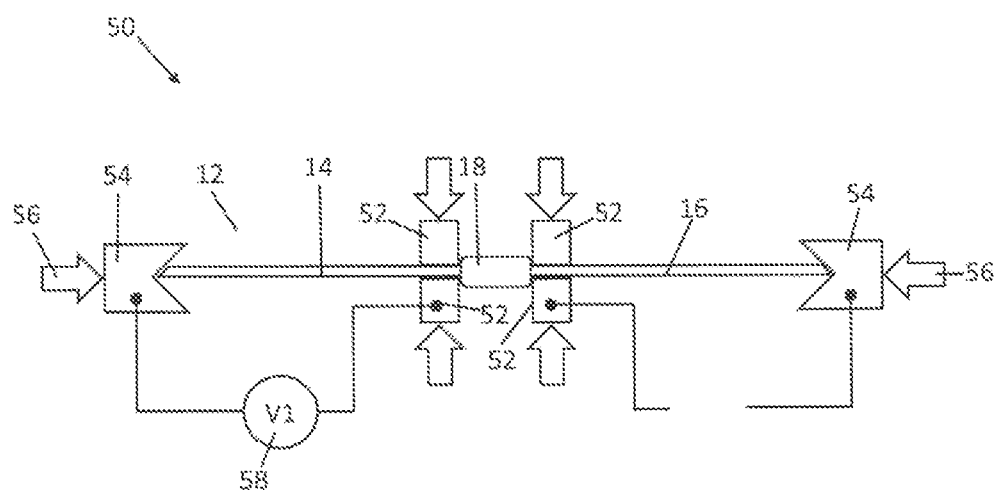
Figure 15:
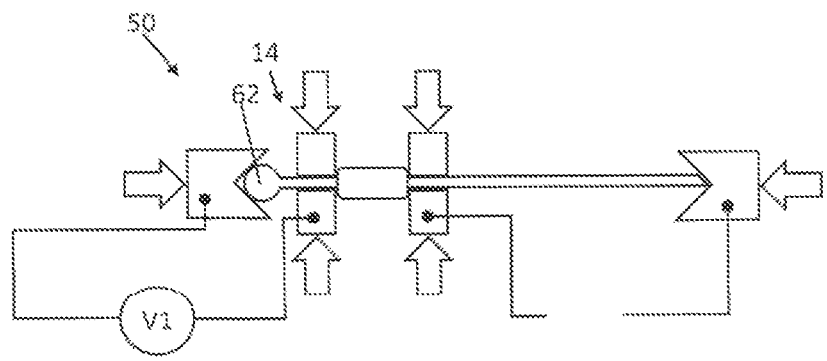

Referring now to FIG. 14 of the drawings, two sets of clamping electrodes 52 are provided—one on either side of the hub 18—so as to provide separate electrical conduction pathways between each end of the needle 14, 16 and a respective pair of tip electrodes 54, which are pushed 56 into axial engagement with their respective needle ends 14, 16. It will be noted that due to this configuration, there is no current pathway through the needle where the hub 18 surrounds the needle 12, and thus, heating of the needle 12 in the vicinity of the hub 18 is minimised.

As shown in FIG. 14 of the drawings, a first voltage V1, 58 is applied between one set of clamping electrodes 52 and its respective tip electrode 54 (the left-hand set in the drawing) and the axial compression 56 applied. The result is the first end of the needle 14 being melted into a blunt, rounded ball 62 in the manner previously described. At this stage, the right-hand side of the system is in an open circuit condition, that is to say without a voltage being applied between the right-hand clamping electrodes 52 and the right-hand tip electrode 54.

Figure 16:
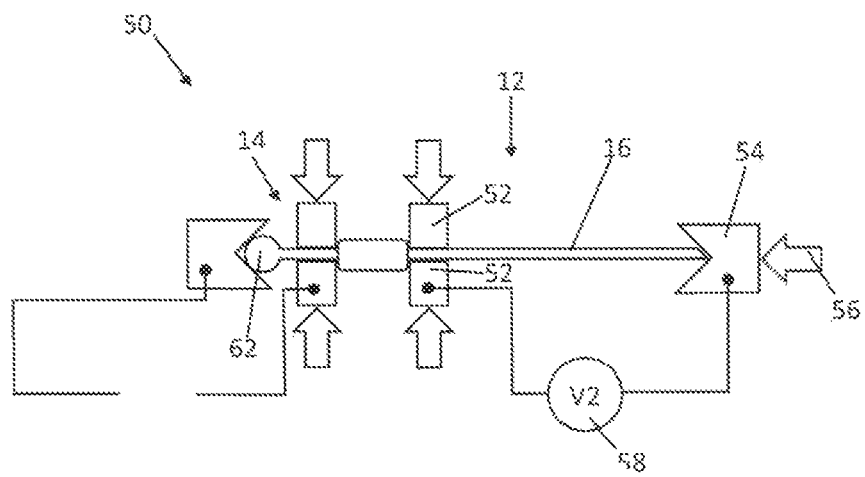
Figure 17:
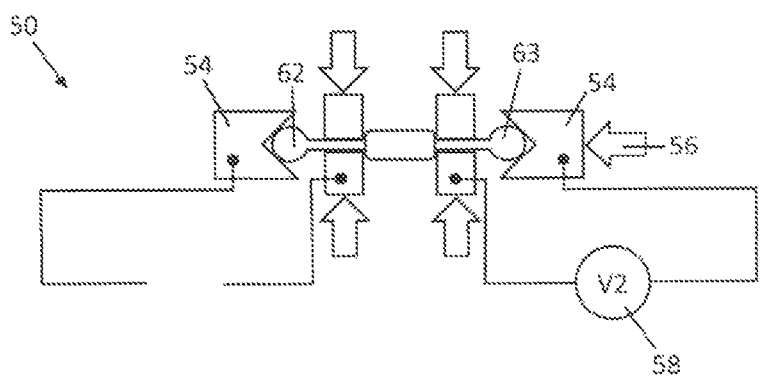
Figure 18:
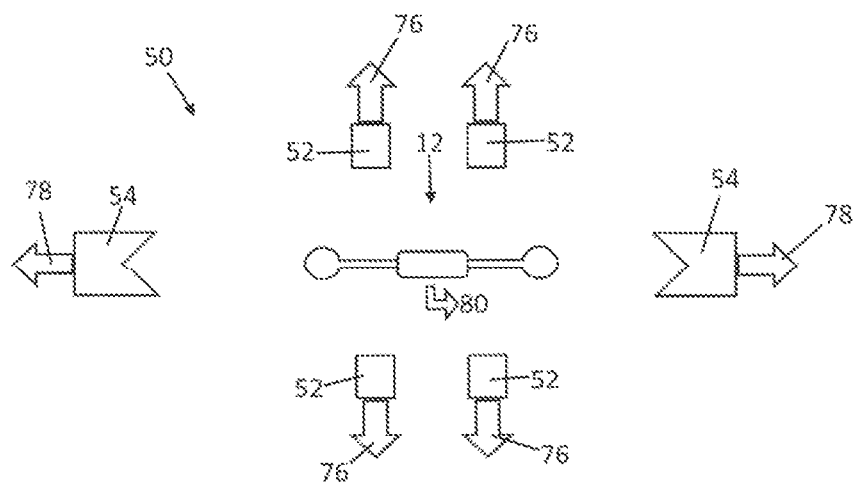

Turning now to FIG. 16, V1 is disconnected and a second voltage V2, 58 is now applied to the clamping electrodes 52 and the tip electrode 54 on the right-hand side, namely at the second end 16 of the needle 12. The axial compression 56, combined with the voltage 58 applied causes the second end 16 of the needle 12 to be melted into a blunt ball 63 as shown in FIG. 17 of the drawings.

Once both ends of the needle have been melted into respective, blunt balls, 62, 63, the tip electrodes 54 can be withdrawn 78 and the clamping electrodes 52 retracted 76 thereby freeing/releasing the needle 12 for subsequent disposal in a waste stream 80, as previously described.

Figure 19:
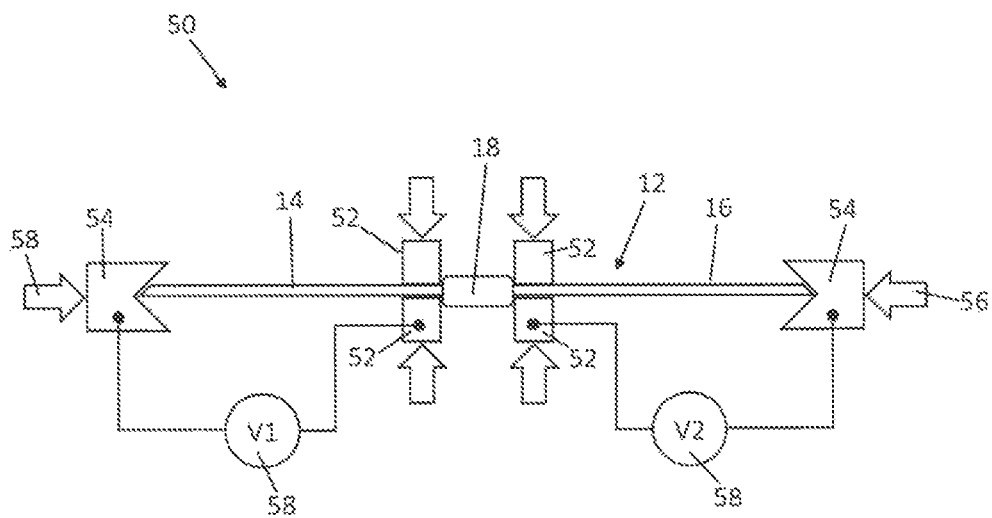
FIGS. 19 and 20 show a variation of the destruction method described in relation to FIGS. 13 to 18 previously.
Figure 20:
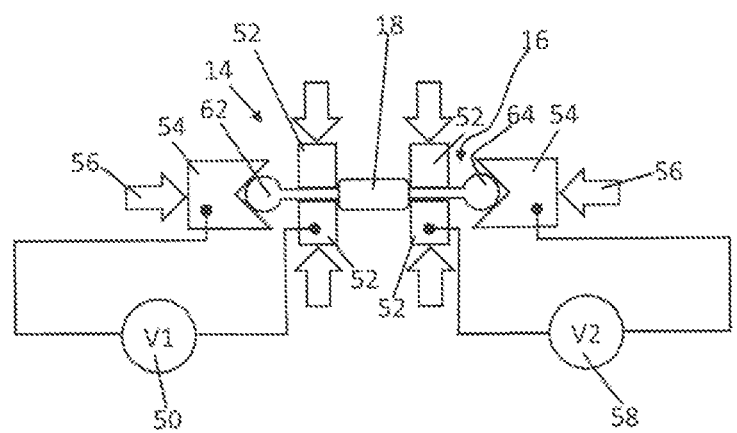

A yet further variation of the needle destruction method previously described is shown in FIGS. 19 and 20 of the accompanying drawings, in which FIG. 19 shows substantially the same set up to that shown in FIG. 14 of the drawings and, therefore, identical reference signs have been used to identify identical features to avoid unnecessary repetition herein.

The difference here is that voltages V1 and V2, 58 are applied simultaneously such that both ends 12, 14 of the needle 12 are melted into the respective blunt balls 62, 63—as shown in FIG. 20, simultaneously. Because the clamping electrodes 52 are maintained at the same potential, there are two separate current pathways within the needle, namely a first current pathway going from the left-hand clamp electrodes 52, through the first end 14 of the needle 12 and into the left-hand tip electrode 54; and a second current pathway going through the right-hand clamping electrodes 52, the second end 16 of the needle 12 and the right-hand tip electrode 54.

Because the potentials of both sets of the clamping electrodes 52 are the same, there is very little, or zero current flowing through the needle 12 in the region of the hub, and this avoids, or reduces the likelihood of the hub getting too hot or catching fire during the process.

In a yet further possible embodiment of the invention, voltages V1 and V2 are pulsed, and are applied alternately such that only one of the aforesaid current paths is in operation at any given moment in time. This also avoids current passing through the needle in the region of the hub, thereby potentially causing the hub 18 to heat and/burn and this is a further possible benefit of the invention.

Figure 21:
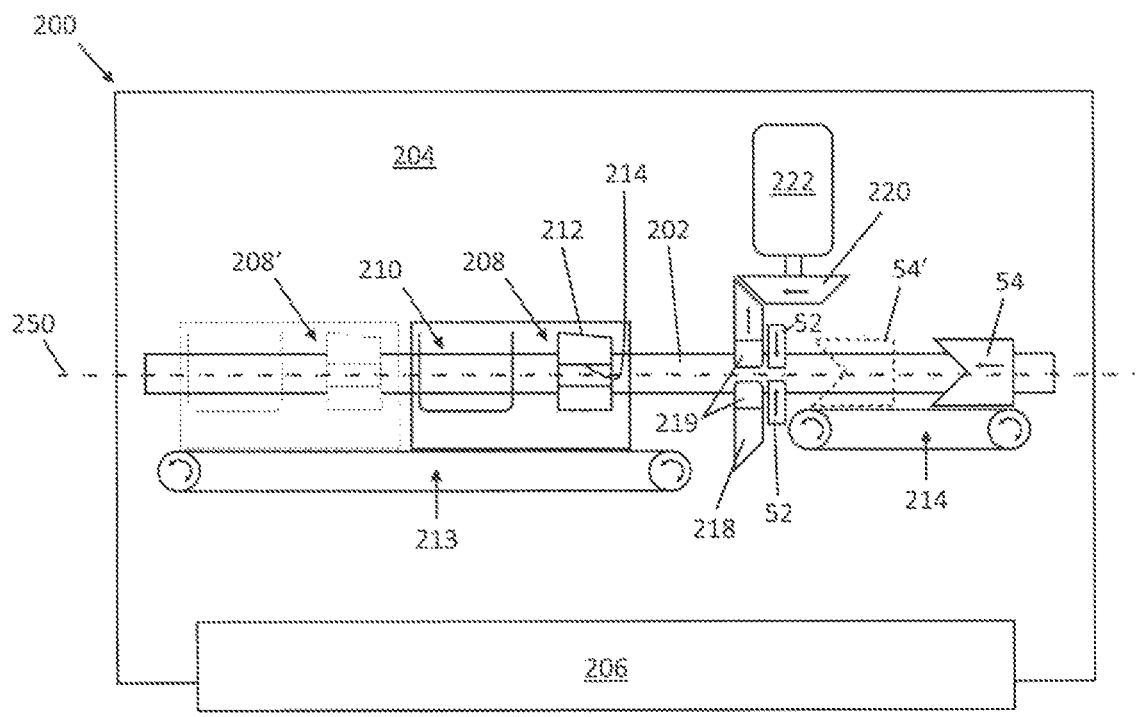
FIG. 21 is a schematic side view of a phlebotomy needle destructions apparatus in accordance with the invention.

FIG. 21 of the drawings is a schematic side view of an apparatus 200 for destroying a phlebotomy needle (not shown). The apparatus 200 comprises a slide rail 202 onto which the various components of the apparatus 200 are slidingly mounted. The slide rail 202 is mounted on a support chassis 204, in this case a vertical board, that is held upright by a base plate 206. The slide rail 202 carries a carriage assembly 208, which has mounted on it, a cradle 210 for holding the cover 20 of a phlebotomy needle, and a turntable 212, which is also rotatably connected to the carriage 208, and which has an internal bore 214 for connecting to the hub 18 of a phlebotomy needle. The carriage 208 is driven by a first pulley mechanism 212 to slide along the slide rail, as indicated by dash lines 208'.

Meanwhile, a hub grip 216 is provided, which is mounted at the centre of a bevel gear 218, which is driven for rotation by a complementary bevel gear 220 and by a motor 222.

On the opposite side of the hub grip 216 to the carriage 208, there is provided a set of clamping electrodes 52, which can be moved towards each other so as to clamp the needle 12 in use.

A tip electrode 54 is also slidingly mounted on the slide rail 202 and is driven by a second pulley system 214 so that it can be moved along the slide rail 202 as indicated by 54'.

FIG. 22 shows a little more detail of the view shown in FIG. 21, namely how the cradle 210 and the table 212 can be rotated relative to the carriage 208, which is in-turn driven for linear movement by the first pulley assembly 213.

It can be seen, from FIG. 22, that the cradle 210 is pivotally mounted on an axle 216, which is driven by a gear 218. Likewise, the turntable 212 is mounted on an axle 220 and is driven by a second gear 222. A rack 224 can be arranged to engage with either of the gears, 218, 212 so that when the carriage 208 is driven by the first pulley assembly 213 in either direction, the rack 224 engages with the respective gear 218, 222 to rotate the cradle 210 and/or the turntable 212.

Other means for reorienting the cradle 210 could be provided. In certain embodiments, the means for reorienting the cradle 210 comprises mounting the cradle 210 on an axle or other pivot, which is driven by a DC or stepper motor so that it can be inverted.

Figure 22A:
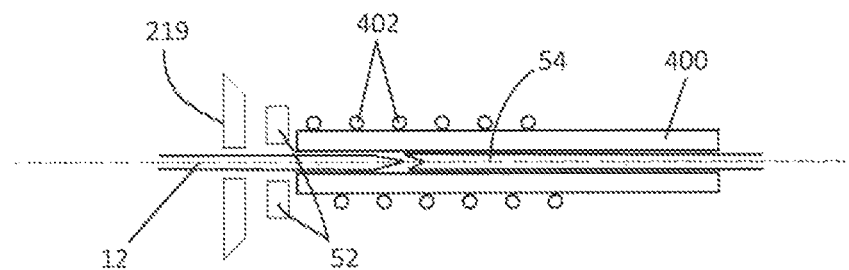
FIG. 22A is a schematic, partial close-up view of the apparatus shown in FIG. 22.

FIG. 22A shows how the apparatus may further comprise a tube 400 for receiving a tip of the needle 12 and within which the tip electrode 52 is arranged to slide. The tube 400 is suitably configured to support the needle 12 and prevent or inhibit it from bowing/bucking during axial compression of the needle. Additionally or alternatively, the tube 400 may be configured to contain the needle as it is melted or softened, and thus prevent discrete droplets of molten needle forming. As the needle gets hot during the melting/destruction procedure, the tube 400 is suitably manufactured of a refractory material, such as quartz. In certain embodiments, a coil 402 surrounds the tube 400. The coil 402 can be any one or more of: a thermostatically-controlled heating coil surrounding the tube for pre-heating the tube and/or needle prior to melting the needle; and an induction coil surrounding the tube for pre-heating and/or heating or melting the needle. Either may be useful for driving-off or evaporating moisture from within the tube 400 and/or the internal bore of the needle, which often contains blood or other fluids, which might adversely affect the melting of the needle into a contiguous ball during the destruction process. The latter may be used to assist in the melting of the needle into a blunt ball.

Figure 23:
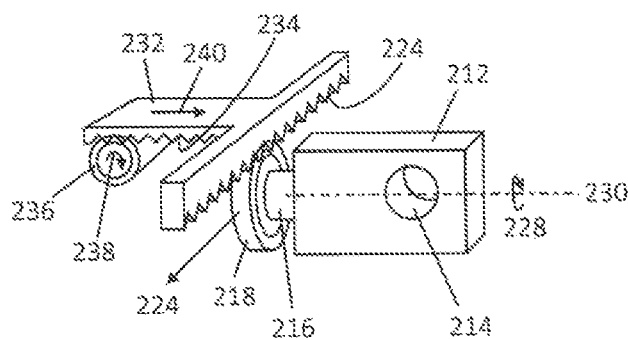
FIGS. 23 and 24 are schematic perspective views of a rotation mechanism for rotating the needle.
Figure 24:
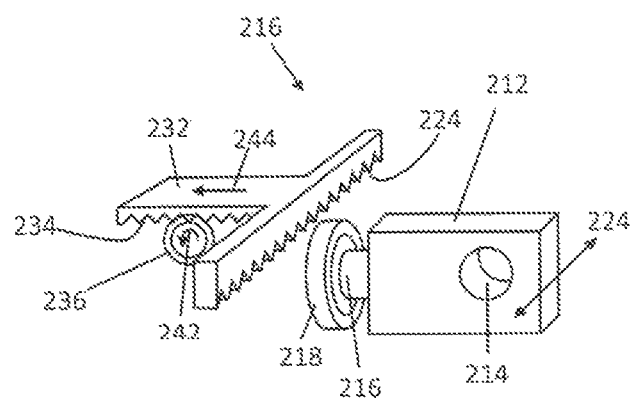

Referring to FIGS. 23 and 24 of the drawings, which show the assembly for the turntable 212, the rack 224 is supported by the main body portion 232, which can be driven by a further rack 234 and pinion 236 towards 240 the gear 218. As the carriage 208 is advanced 224, the teeth of the rack 224 engage with the teeth of the gear 218 to cause the turntable 212 to rotate 228 about an axis 230.

Referring to FIG. 24, when the main body 232 is retracted 244, the rack 223 no longer 10 engages with the gear 218, and so linear movement 224 of the carriage 208 no longer causes the turntable 212 to rotate.

It will be appreciated that the same, or different, racks 224 can be used to actuate either gear 218, 222 and so effect independent or co-ordinated rotation of the cradle 210 and turntable 212, as required. In other embodiments, the axles 216, 220 are directly driven, for example, by motors.

Figure 25:
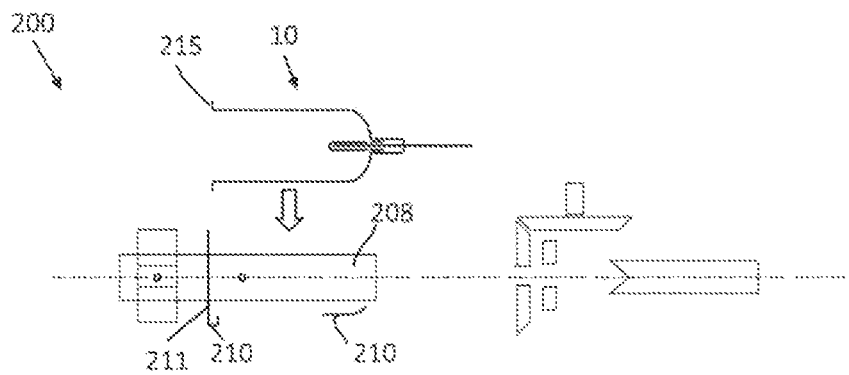

The sequence of operation of the apparatus 200 is shown in FIGS. 25 to 44 of the drawings as follows:

In FIG. 25, the apparatus 200 is in an, initial start position with the carriage 208 retracted and the cradle 210 being oriented upright for receiving a phlebotomy needle 10, which can simply be dropped into the cradle 210. The cradle 210 has an end 211, which engages formations 215 of the phlebotomy needle 10 so as to hold it in position, axially relative to the cradle 210.

Figure 26:
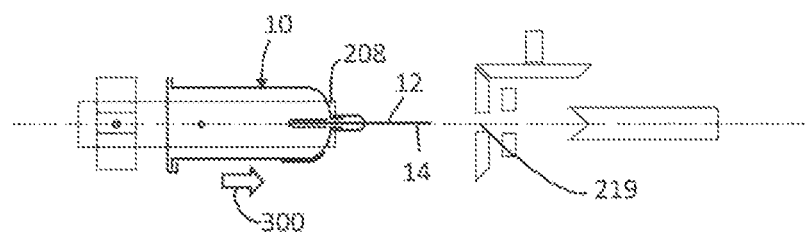
Figure 27:
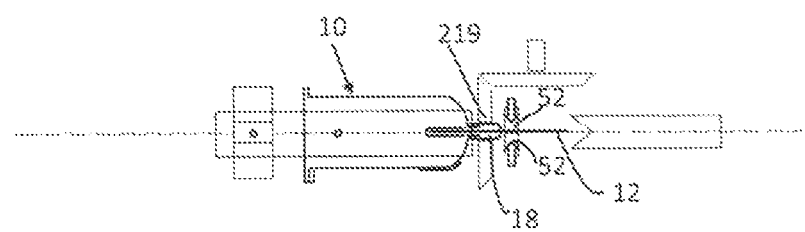

In FIG. 26, it can be seen that the carriage 208 can be advanced 300 (using the first pulley assembly 213) such that the first tip 14 of the phlebotomy needle 12 passes through the hub grip 219, as shown in FIG. 27 at which point, the hub grip 219 frictionally engages the hub 18 of the phlebotomy needle 10.

As shown in FIG. 27, the clamping electrodes 52 are moved in towards each other so as to grip the needle 12.

Figure 28:
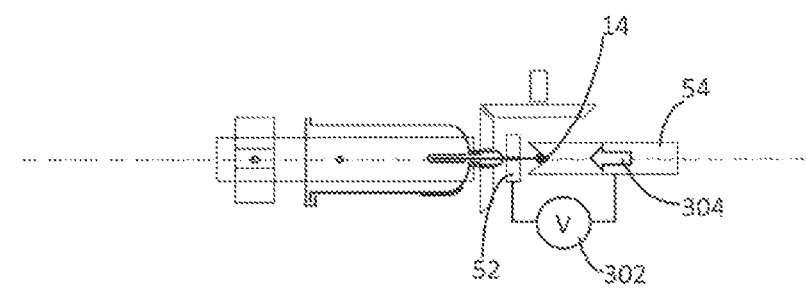

Referring now to FIG. 28 of the drawings, voltage 302 is then applied between the clamping electrodes 54 and the tip electrode 54, so as to soften and blunten the tip 14 of the needle into a ball, as previously described. The tip electrode 54 is advanced 304 throughout this process, and as previously described, "destroys" the first end of the needle 12.

Figure 29:
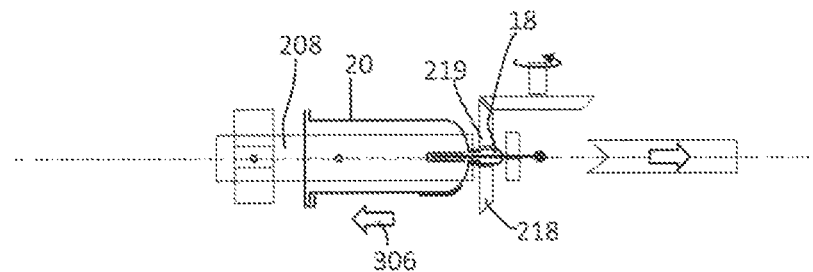

Next, as shown in FIG. 29, the hub grip 219 is rotated so whilst the carriage 208 is retracted 306. This unscrews the cover 20 from the hub 18, which means that, as shown in FIG. 30, when the carriage is fully-retracted, the needle 12 is thus separated from the cover 20.

Figure 30:
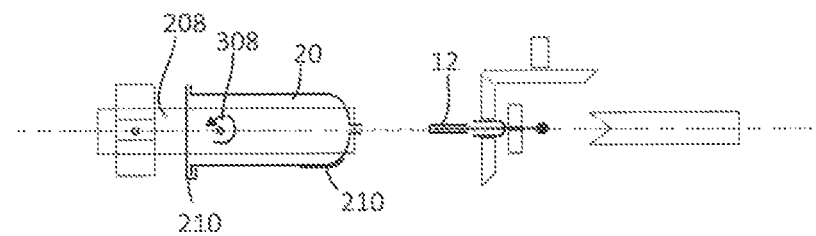
Figure 31:
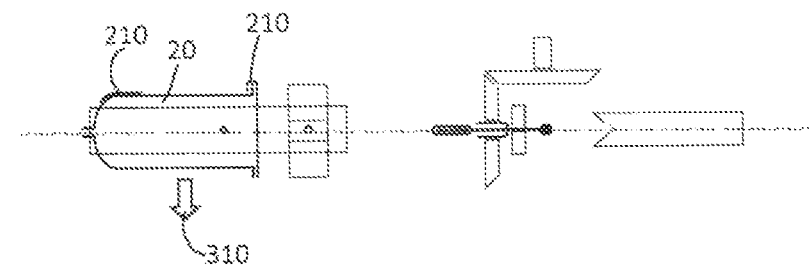

As shown in FIGS. 30 and 31, the cradle 210 is then rotated 308 to the position shown in FIG. 31, where the cover 20 then drops away 310 into a waste bin (not shown).

Figure 32:
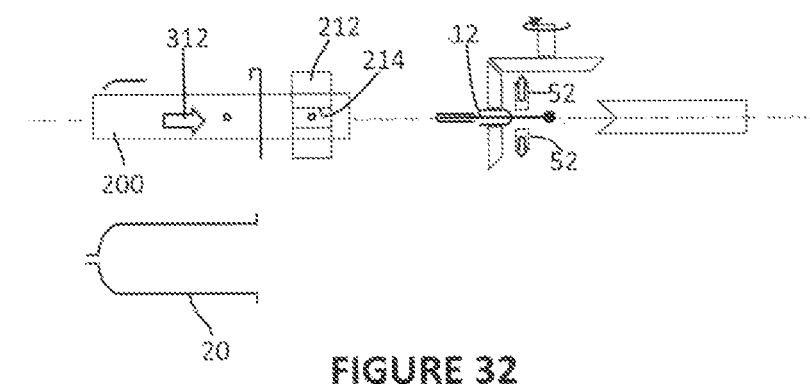
Figure 33:
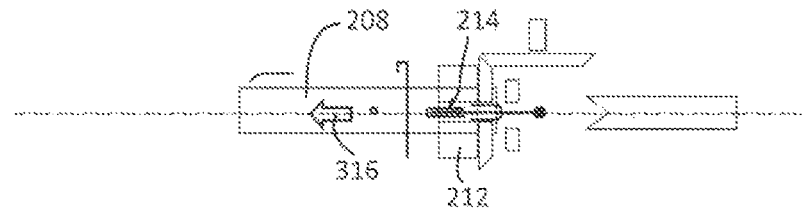

The next stage in the procedure, as shown in FIG. 32, involves rotating the needle 12 using the motor 222 and hub grip 219, whilst releasing the clamping electrodes 52 and advancing 312 the carriage 208. When the turntable 212 reaches the hub 18, as shown in FIG. 33, the screw thread on the hub, which previously retained the cover 20, now engages with a screw thread in the bore 214 of the turntable 212.

Figure 34:
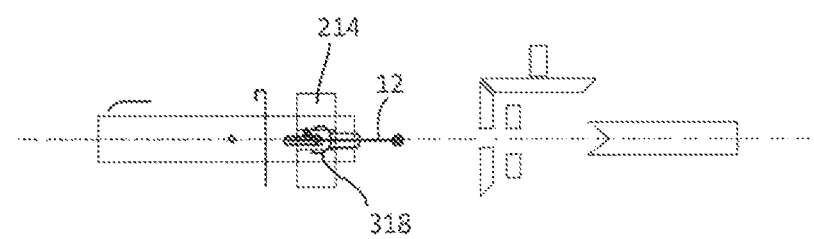
Figure 35:
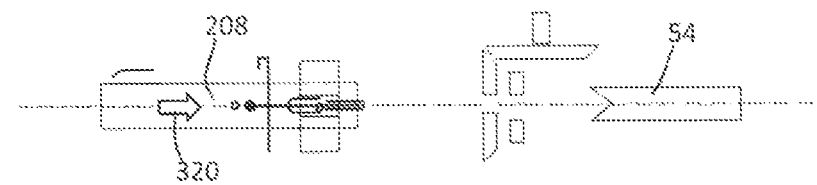

The carriage 208 can now be retracted 316 to the position shown in FIG. 34, and the turntable 214 rotated 318 so as to present the opposite end of the needle 12 to the tip electrode 54, as shown in FIG. 35.

Figure 36:
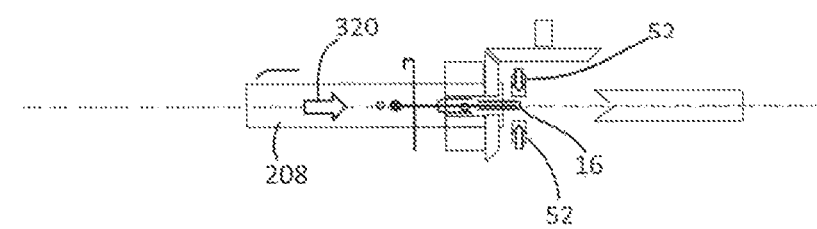
Figure 37:
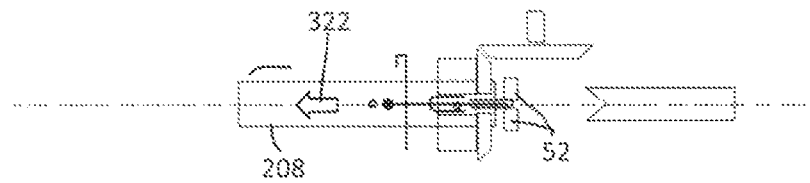

Advancing 320 the carriage 208 again results in a configuration shown in FIG. 36—where the rubber cover 16 is now extending into the "needle destruction" part of the device 200 where it can be gripped by the clamping electrodes 52 as shown in FIG. 37.

Figure 38:
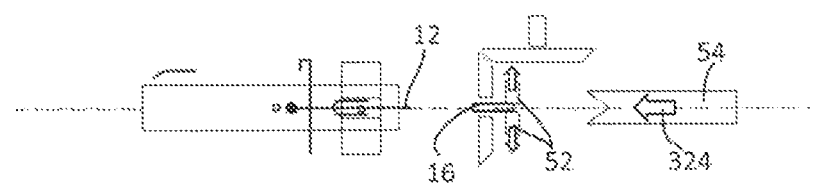
Figure 39:
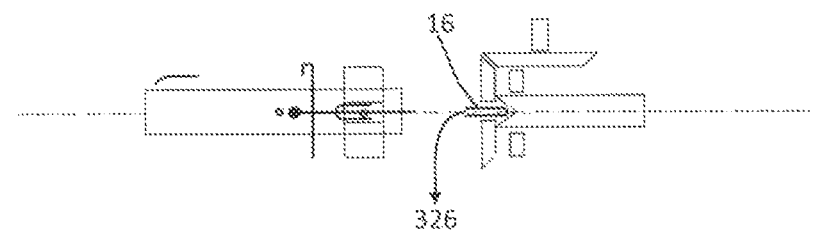
Figure 40:

The next stage in the process involves retracting 222 the carriage 208 once again so as to separate the rubber cover 16 (now gripped by the clamping electrodes 52) from the second end of the needle 12, as shown in FIG. 38.

Meanwhile, the tip electrode 54 is advanced 324, once the clamping electrodes 52 have been re-opened, so as to push/eject 326 the rubber cover 16 into another waste bin (not shown).

Figure 41:
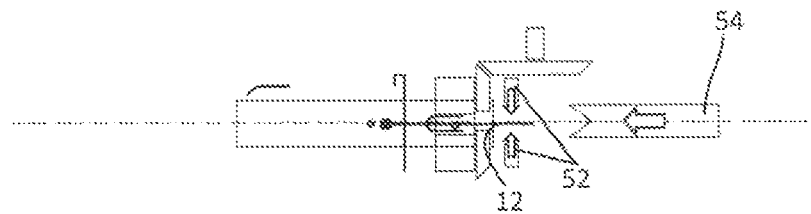
Figure 42:
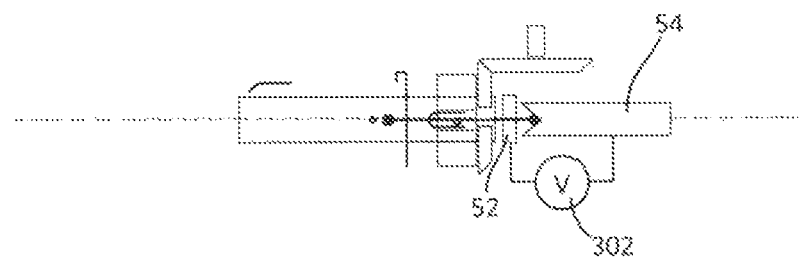

The procedure continues by the carriage 208 being advanced 326 once again so that the second end of the needle 12 lies between the clamping electrodes 52, as shown in FIG. 41, where the tip electrode 54 can be advanced once again towards the needle 12 so as to destroy it.

As shown in FIG. 42, this is once again achieved by applying a voltage 302 between the clamping electrodes 52 and the tip electrode 54, whilst advancing the tip electrode in the afore-described manor. This softens and blunts the second end of the needle 12 into a blunt ball, as previously described.

Figure 43:
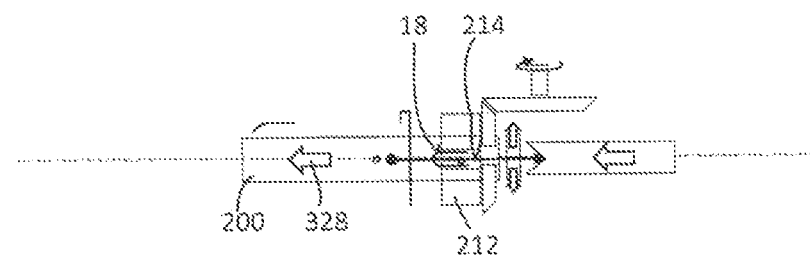
Figure 44:
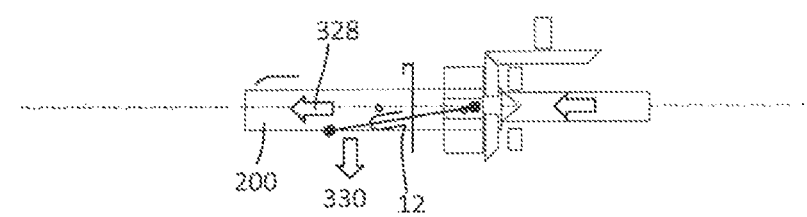

The final stages of the procedure are shown in FIGS. 43 and 44 of the drawings, where the motor 222 is rotated again so as to unscrew the hub 18 from the bore 214 of the turntable 212, thereby releasing it. Retraction 328 of the carriage 208 results in the destroyed needle 12 falling away 330 into a further waste collection receptacle (not shown).

The invention is not restricted to the details of the foregoing embodiment(s) which are merely exemplary. For example, a containment cylinder or a heated containment cylinder may be placed around the needle during its axial compression to prevent it from buckling under the application of an axial stress; and the order of the processing steps may be altered without departing from the scope of the invention. Further, whilst one embodiment of the invention has been described, which uses a linear actuator and a turntable, this is just an example, and is not limiting of the invention. For example, the same or a similar process may be performed using a carousel—or other type of arrangement, where each processing step is carried out in sequence, at different positions. The materials and any dimensions mentioned herein are exemplary only and are not necessarily intended to limit the scope of this disclosure, except where necessary for a particular function to work.

The invention claimed is:

1. An apparatus for processing a phlebotomy needle, the phlebotomy needle including a double-ended needle having a first end terminating in a tip and a second end terminating in a second tip, and a hub affixed to the needle at a location between the first tip and the second tip, the apparatus comprising:
   a clamping electrode for contacting and clamping one end of the needle between the hub and the tip;
   a tip electrode for contacting the needle at tip, the tip electrode being configured to receive an axial force towards the hub and parallel to an axis of the needle to compress and blunt the tip of the needle;
   means for applying a voltage between the clamping electrode and the tip electrode, such that an electric current passes through the end of the needle between the clamping electrode and the tip electrode, which current results, in use, resistive/Ohmic heating, which heats and softens or melts the tip of the needle; and
   means for selectively orienting the needle in a first and a second position:
      the first position being a position in which the clamping electrode clamps the first end of the needle between the hub and the first tip and in which the tip electrode contacts the first tip, and
      the second position being a position in which the clamping electrode clamps the second end of the needle between the hub and the second tip and in which the tip electrode contacts the second tip.

2. The apparatus of claim 1, wherein the means for selectively orienting the needle comprises a turntable adapted to connect to the hub and to rotate through substantially 180-degrees about a point lying substantially on the axis of the needle.

3. The apparatus of claim 2, wherein the turntable comprises a main body with a through bore whose axis is coaxial with the axis of the needle, the through bore being adapted to connect to the hub of the needle.

4. The apparatus of claim 3, wherein the through bore is internally screw-threaded to screw-threadingly engage with an external screw thread of the hub.

5. The apparatus of claim 1, wherein the phlebotomy needle further comprises a main body affixed to the hub, and
   the apparatus further comprising a cradle for supporting the main body, the cradle being arranged to support the main body such that the axis of the needle is aligned a with centre of the tip electrode.

6. The apparatus of claim 5, wherein any one or more of the turntable, the cradle and the tip electrode is mounted on a linear slide, which permits the needle to be displaced along a locus that is coaxial with the axis of the needle.

7. The apparatus of claim 6, wherein the turntable, cradle and/or tip electrode is displaced on the linear slide by a linear actuator or a pulley arrangement.

8. The apparatus of claim 5, further comprising a pivot driven by a motor to invert the cradle to release the main body therefrom.

9. The apparatus of claim 1, further comprising a hub grip interposed between the means for selectively orienting the needle and the tip electrode, the hub grip being coaxial with the axis of the needle, adapted to frictionally engage the hub.

10. The apparatus of claim 9, wherein the main body is detachable from the hub by gripping the hub in the hub grip, and by linearly displacing the cradle relative to the hub grip so as to slide or shear the main body off the hub.

11. The apparatus of claim 9, wherein the hub grip further comprises means for rotating the hub grip about the axis of the needle, and wherein the main body is detachable from the hub by gripping the hub in the hub grip, by rotating the hub grip, and optionally by linearly displacing the cradle so as to unscrew the main body from the hub.

12. The apparatus of claim 1, wherein an end of the needle comprises a cover, and wherein the cover is detachable from the needle by the steps of:
   displacing the needle such that the cover is positioned between the clamping electrodes;
   moving the clamping electrodes towards one another so as to grip the cover therebetween; and
   linear displacement of the needle away from the clamping electrodes so as to slide or shear the cover from the needle.

13. The apparatus of claim 12, further comprising the steps of:
   moving the clamping electrodes apart; and
   moving the tip electrode so as to remove the cover from between the clamping electrodes.

14. The apparatus of claim 1, further comprising a tube for receiving a tip of the needle and within which the tip electrode is arranged to slide, the tube being configured to support the needle and prevent or inhibit bowing/bucking thereof during axial compression of the needle by containing the needle as it is melted or softened, and thus prevent discrete droplets of molten needle forming.

15. The apparatus of claim 14, further comprising a thermostatically-controlled heating coil surrounding the tube for pre-heating the tube prior to melting the needle.

16. The apparatus of claim 14, further comprising an induction coil surrounding the tube for pre-heating and/or heating or melting the needle.

17. The apparatus of claim 1, wherein the clamping electrode comprises a pair of opposing metal jaws which move towards each other so as to clamp a portion of the needle therebetween.

18. The apparatus of claim 1, wherein the clamping electrode clamps the needle at any one or more of the positions from the group comprising: within 10 mm of the hub; within 5 mm of the hub; within 2 mm of the hub; within 1 mm of the hub; and more than 1 mm from the hub.

19. The apparatus of claim 1, wherein the tip electrode comprises a concave surface for centralising the tip of the needle therewith.

20. The apparatus of claim 1, wherein the means for applying a voltage comprises any one or more of the group comprising: a DC power supply, an AC power supply, and an RF power supply, the AC, DC or RF power supply is adapted to apply a pulsed voltage between the clamping and tip electrodes, and optionally wherein the AC, DC or RF power supply is adapted to alternately apply a voltage: between the first clamping and first tip electrodes, and between the second clamping and second tip electrodes.

* * * * *